US009532746B2

(12) United States Patent
Thakur et al.

(10) Patent No.: US 9,532,746 B2
(45) Date of Patent: Jan. 3, 2017

(54) MULTIPLE VECTOR FLUID LOCALIZATION

(71) Applicant: Cardiac Pacemakers, Inc., St. Paul, MN (US)

(72) Inventors: Pramodsingh Hirasingh Thakur, Woodbury, MN (US); Abhilash Patangay, Inver Grove Heights, MN (US); Kent Lee, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/538,153

(22) Filed: Nov. 11, 2014

(65) Prior Publication Data

US 2015/0065819 A1 Mar. 5, 2015

Related U.S. Application Data

(63) Continuation of application No. 12/912,219, filed on Oct. 26, 2010, now Pat. No. 8,900,140.

(60) Provisional application No. 61/255,360, filed on Oct. 27, 2009.

(51) Int. Cl.
| | |
|---|---|
| *A61B 5/00* | (2006.01) |
| *A61B 5/01* | (2006.01) |
| *A61N 1/36* | (2006.01) |
| *A61B 5/053* | (2006.01) |
| *A61N 1/365* | (2006.01) |
| *A61N 1/37* | (2006.01) |
| *A61N 1/362* | (2006.01) |

(52) U.S. Cl.
CPC .............. *A61B 5/4878* (2013.01); *A61B 5/01* (2013.01); *A61B 5/053* (2013.01); *A61B 5/4875* (2013.01); *A61B 5/6869* (2013.01); *A61B 5/7282* (2013.01); *A61N 1/36521* (2013.01); *A61N 1/3702* (2013.01); *A61N 1/3627* (2013.01)

(58) Field of Classification Search
CPC ......... A61B 5/01; A61B 5/053; A61B 5/4875; A61B 5/4878; A61B 5/6869; A61B 5/7282; A61N 1/3627; A61N 1/36521; A61N 1/3702
USPC ............... 600/300, 301, 345, 483, 484, 506, 528, 600/529; 607/5, 9, 17, 27
See application file for complete search history.

(56) References Cited

U.S. PATENT DOCUMENTS

| | | |
|---|---|---|
| 5,957,861 A | 9/1999 | Combs et al. |
| 6,282,444 B1 | 8/2001 | Kroll et al. |
| 6,512,949 B1 | 1/2003 | Combs et al. |
| 7,130,679 B2 | 10/2006 | Parsonnet et al. |

(Continued)

OTHER PUBLICATIONS

U.S. Appl. No. 12/912,219 , Response filed Oct. 11, 2013 to Non Final Office Action mailed Jul. 18, 2013, 18 pgs.

(Continued)

*Primary Examiner* — Christopher A Flory
(74) *Attorney, Agent, or Firm* — Schwegman Lundberg & Woessner P.A.

(57) ABSTRACT

A differential or relative measurement between an orthogonal measurement vector and another measurement vector can be used to determine the location where fluid accumulation is occurring or the local change in such fluid accumulation. This can help diagnose or treat infection or hematoma or seroma at a pocket of an implanted cardiac rhythm management device, other implanted medical device, or prosthesis. It can also help diagnose or treat pulmonary edema, pneumonia, pulmonary congestion, pericardial effusion, pericarditis, pleural effusion, hemodilution, or another physiological condition.

20 Claims, 5 Drawing Sheets

(56) References Cited

U.S. PATENT DOCUMENTS

| | | |
|---|---|---|
| 7,149,573 B2 | 12/2006 | Wang |
| 7,228,174 B2 | 6/2007 | Burnes et al. |
| 7,305,266 B1 | 12/2007 | Kroll |
| 7,376,463 B2 | 5/2008 | Salo et al. |
| 7,630,763 B2 | 12/2009 | Kwok et al. |
| 7,682,355 B2 | 3/2010 | Gerber et al. |
| 7,764,996 B2 | 7/2010 | Zhang et al. |
| 7,938,782 B2 | 5/2011 | Stahmann et al. |
| 7,981,042 B2 | 7/2011 | Stahmann et al. |
| 8,032,212 B2 | 10/2011 | Bornzin et al. |
| 8,900,140 B2 | 12/2014 | Thakur et al. |
| 2002/0177823 A1 | 11/2002 | Prosl et al. |
| 2004/0102712 A1 | 5/2004 | Belalcazar et al. |
| 2004/0215097 A1 | 10/2004 | Wang |
| 2005/0080460 A1 | 4/2005 | Wang et al. |
| 2006/0017575 A1 | 1/2006 | McAdams |
| 2006/0167502 A1 | 7/2006 | Haefner |
| 2006/0264775 A1 | 11/2006 | Mills et al. |
| 2007/0118180 A1 | 5/2007 | Ni et al. |
| 2008/0064980 A1 | 3/2008 | Lee et al. |
| 2008/0091114 A1 | 4/2008 | Min et al. |
| 2008/0125826 A1 | 5/2008 | Belalcazar et al. |
| 2008/0132802 A1 | 6/2008 | Ni et al. |
| 2008/0215108 A1 | 9/2008 | Zhu et al. |
| 2008/0262322 A1 | 10/2008 | Gerber et al. |
| 2008/0262361 A1 | 10/2008 | Gutfinger et al. |
| 2009/0012416 A1 | 1/2009 | Belalcazar et al. |
| 2009/0082652 A1 | 3/2009 | Koh et al. |
| 2009/0131999 A1 | 5/2009 | Li et al. |
| 2009/0132000 A1 | 5/2009 | Brockway et al. |
| 2010/0280500 A1 | 11/2010 | Skelton et al. |
| 2011/0098771 A1 | 4/2011 | Thakur et al. |

OTHER PUBLICATIONS

U.S. Appl. No. 12/912,219, Advisory Action mailed Dec. 24, 2013, 3 pgs.

U.S. Appl. No. 12/912,219, Final Office Action mailed Aug. 31, 2012, 13 pgs.

U.S. Appl. No. 12/912,219, Final Office Action mailed Nov. 8, 2013, 12 pgs.

U.S. Appl. No. 12/912,219, Non Final Office Action mailed Feb. 24, 2014, 12 pgs.

U.S. Appl. No. 12/912,219, Non Final Office Action mailed Apr. 11, 2012, 10 pgs.

U.S. Appl. No. 12/912,219, Non Final Office Action mailed Jul. 18, 2013, 9 pgs.

U.S. Appl. No. 12/912,219, Notice of Allowance mailed Aug. 1, 2014, 8 pgs.

U.S. Appl. No. 12/912,219, Respnse filed Dec. 12, 2013 to Final Office Action mailed Nov. 8, 2013, 16 pgs.

U.S. Appl. No. 12/912,219, Response filed May 22, 2014 to Non Final Office Aciton mailed Feb. 24, 2014, 14 pgs.

U.S. Appl. No. 12/912,219, Response filed Dec. 21, 2012 to Final Office Action mailed Aug. 31, 2012, 17 pgs.

U.S. Appl. No. 12/912/219, Response filed Jul. 10, 2012 to Non Final Office Action mailed Apr. 11, 2012, 25 pgs.

"Automated Device Impedence Vector Switching", IP.com, http://www.ip.com/pubview/IPCOM000170612D, (May 22, 2008), 10 pgs.

Belalcazar, Hugo Andres, "Optimal Electrode Configurations for Implantable Monitoring of Pulmonary Edema", A Dissertation Submitted to the Faculty of the Graduate School of the University of Minnesota, (Dec. 2004), 327 pgs.

Cacoub. P., et al., "Pacemaker infective endocarditis", Am J Cardiol., 82(4), (Aug. 15, 1998), 480-4.

Ferguson, T. B, et al., "The additional hospital costs generated in the management of complications of pacemaker and defibrillator implantations.", J Thorac Cardiovasc Surg., 111(4), (Apr. 1996), 742-51;discussion 751-2.

Guyton, A. C, et al., "Effect of elevated left atrial pressure and decreased plasma protein concentration on the development of pulmonary edema", Circ Res., 7(4), (Jul. 1959), 649-57.

Klug, D., et al., "Systemic infection related to endocarditis on pacemaker leads: clinical presentation and management", Circulation, 95(8), (Apr. 15, 1997), 2098-107.

Kowalski, M., et al., "Problems with implantable cardiac device therapy.", Cardiol Clin., 26(3), (Aug. 2008), 441-58, vii.

Voigt, A., et al., "Rising rates of cardiac rhythm management device infections in the United States: 1996 through 2003", J Am Coll Cardiol., 48(3), (Aug. 1, 2006), 590-1.

U.S. Appl. No. 15/165,817, Preliminary Amendment filed May 31, 2016, 8 pgs.

MULTIPLE VECTOR FLUID LOCALIZATION

CLAIM OF PRIORITY

This application is a continuation of U.S. application Ser. No. 12/912,219, filed Oct. 26, 2010, now issued as U.S. Pat. No. 8,900,140, which claims the benefit of priority under 35 U.S.C. §119(e) of Thakur et al., U.S. Provisional Patent Application Ser. No. 61/255,360, entitled "MULTIPLE VECTOR FLUID LOCALIZATION", filed on Oct. 27, 2009, each of which is herein incorporated by reference in its entirety.

BACKGROUND

Cardiac rhythm management (CRM) devices can help assist heart function, such as by providing pacing electrostimulations to evoke responsive heart contractions, providing cardiac resynchronization therapy (CRT) electrostimulations to coordinate the spatial nature of a heart contraction of one or more heart chambers, providing antitachyarrhythmia pacing, cardioversion, or defibrillation shocks to interrupt a tachyarrhythmia, or providing neurostimulation to influence sympathetic or parasympathetic nervous system response.

Diagnosing the physiological condition of a patient can involve determining whether fluid accumulation has occurred. For example, congestive heart failure (CHF) patients can have poor cardiac output (CO) from the heart. This can lead to fluid buildup in the lungs (e.g., pulmonary edema) or in the limbs (e.g., peripheral edema). Fluid accumulation status can be monitored by monitoring tissue impedance. Tissue impedance monitoring can involve injecting a test current into the tissue, and monitoring a resulting voltage. The resulting voltage can provide an indication of tissue impedance. The tissue impedance can provide an indication of how wet the tissue is. As the tissue becomes wetter, its impedance decreases.

Wang U.S. Pat. No. 7,149,573 discloses an example of tissue impedance monitoring, including determining contributing physiological impedance factors, such as lung resistivity, blood resistivity, heart muscle resistivity, skeletal muscle resistivity, heart volume and lung volume. (See Wang '573 at Abstract.) Wang's impedance determination apparently relies upon parallel vectors—Wang's test current is injected between electrodes defining a test current vector therebetween, and the resulting voltage is measured between electrodes defining a response voltage vector therebetween, and the response voltage vector is substantially parallel in direction to the test current vector. (See, e.g., Wang '573 at col. 9, lines 30-60.)

OVERVIEW

The present inventors have recognized, among other things, that determining using a parallel vector approach to determine fluid accumulation can provide only limited sensitivity, which can make it more difficult to determine whether fluid accumulation is present, the degree to which fluid accumulation is present, whether the fluid accumulation is increasing or decreasing, or the particular localized region experiencing the fluid accumulation. The present inventors have also recognized, among other things, that localizing the particular region experiencing the fluid accumulation can be a helpful diagnostic. For example, the present inventors have recognized that discriminating between different regions to determine which region is experiencing fluid accumulation, which region is experiencing more (or less) fluid accumulation, or the relative degree of fluid accumulation or change in fluid accumulation between the regions, can provide helpful diagnostic information to a physician or an automated medical device, allowing therapy to be selected or adjusted accordingly. The present inventors have recognized that this, in turn, can enhance patient care, such as of CHF or other patients.

The present inventors have also recognized, among other things, that using (1) an orthogonal measurement vector and (2) a non-orthogonal measurement vector, a relative measurement between (1) and (2) can be used to provide a more sensitive indication of fluid accumulation. An orthogonal measurement vector can be conceptualized as including an excitation vector defined by excitation electrodes that are used to provide the excitation signal, and a response vector defined by response electrodes that are used to sense a response to the excitation signal, wherein the response vector is substantially orthogonal to the excitation vector. The present inventors have further recognized that this more sensitive relative measurement can be used to localize a region of fluid accumulation, or to distinguish between different regions of fluid accumulation. As illustrative examples, this can be useful to diagnose, or to discriminate between:

- fluid accumulation localized at a "pocket" or like region at which an implantable CRM device or other implantable medical device (IMD) or prosthesis is located, such as can result from infection, hematoma, or seroma;
- fluid accumulation localized in the lungs, such as can result from pulmonary edema, pneumonia, or pulmonary congestion;
- global fluid accumulation (e.g., in the lungs and elsewhere), such as can result from an acute decompensation episode as sometimes experienced by a CHF patient;
- fluid accumulation around the heart (e.g., pericardial effusion, during the early stages of which fluid accumulation occurs in the pericardial sac around the heart such as near the apex of the heart); or
- hemodilution, which constitutes a decreased concentration of cells and solids in the blood resulting from gain of fluid.

Example 1 can include subject matter that can include a first interface, configured to be coupled to implantable first electrodes configured to define a first measurement vector, within a subject, comprising a first excitation vector for providing a first excitation signal and a first response vector for sensing a first response to the first excitation signal. A second interface can be configured to be coupled to implantable second electrodes configured to define a second measurement vector, within the subject, comprising a second excitation vector for providing a second excitation signal and a second response vector for sensing a second response to the second excitation signal, wherein the second excitation vector is substantially orthogonal to the second response vector. A tissue characteristic measurement circuit, selectively communicatively coupled to the first and second electrodes, and configured to repeatedly perform a first tissue characteristic measurement using the first measurement vector and to perform a second tissue characteristic measurement using the second measurement vector. A processor can be communicatively coupled to the tissue characteristic measurement circuit, the processor configured to use information about a change in the first tissue characteristic measurement over a period of time and information about a change in the second tissue characteristic measurement over the period of time to provide an indication associated with how much fluid is present at an first location in the subject relative to how much fluid is present at a second location in the subject.

In Example 2, the subject matter of Example 1 can optionally further include the implantable first electrodes and the implantable second electrodes.

In Example 3, the subject matter of any one of Examples 1-2 can optionally include the processor being configured to use the information about the change in the first tissue characteristic measurement over the period of time and the information about the change in the second tissue characteristic measurement over the period of time to provide an indication associated with how much fluid is present at the first location, wherein the first location is associated with a pocket about an implantable medical device, relative to how much fluid is present at the second location, wherein the second location is within the subject but separated from the pocket about the implantable medical device.

In Example 4, the subject matter of any one of Examples 1-3 can optionally include the processor being configured to use the information about the change in the first tissue characteristic measurement over the period of time and the information about the change in the second tissue characteristic measurement over the period of time to provide an indication of whether infection is present at the first location associated with the pocket about the implantable medical device.

In Example 5, the subject matter of any one of Examples 1-4 can optionally include a first temperature sensor configured to be associated with the subject, and wherein the processor is configured to be communicatively coupled to the first temperature sensor to receive information about a first temperature at a location of the subject associated with the first temperature sensor, and to use the information about the first temperature to provide the indication of whether infection is present at the first location associated with the pocket about the implantable medical device.

In Example 6, the subject matter of any one of Examples 1-5 can optionally include a second temperature sensor configured to be associated with the subject at a different location than the first temperature sensor, and wherein the processor is configured to be communicatively coupled to the second temperature sensor to receive information about a second temperature at a location of the subject associated with the second temperature sensor, and to use the information about a difference between the second temperature and the first temperature to provide the indication of whether infection is present at the first location associated with the pocket about the implantable medical device.

In Example 7, the subject matter of any one of Examples 1-6 can optionally include the second measurement vector including a second excitation vector for providing a second excitation signal between a left ventricular electrode configured to be associated with a left ventricle and a pectoral electrode configured to be associated with a pectoral region, and a second response vector for sensing a second response to the second excitation signal between a left ventricular electrode configured to be associated with a left ventricle and a right atrial electrode configured to be associated with a right atrium, wherein the second excitation vector is substantially orthogonal to the second response vector.

In Example 8, the subject matter of any one of Examples 1-7 can optionally include at least one of: (a) the first measurement vector comprising a first excitation vector for providing a first excitation signal between a right ventricular electrode configured to be associated with a right ventricle and a pectoral electrode configured to be associated with a pectoral region, and a first response vector for sensing a first response to the first excitation signal, the sensing the first response using a right ventricular electrode configured to be associated with a right ventricle and a pectoral electrode configured to be associated with a pectoral region; (b) the first measurement vector comprising a first excitation vector for providing a first excitation signal between a right atrial electrode configured to be associated with a right atrium and a pectoral electrode configured to be associated with a pectoral region, and a first response vector for sensing a first response to the first excitation signal, the sensing the first response using a right atrial electrode configured to be associated with a right atrium and a pectoral electrode configured to be associated with a pectoral region; or (c) the first measurement vector comprising a first excitation vector for providing a first excitation signal between a left ventricular electrode configured to be associated with a left ventricle and a pectoral electrode configured to be associated with a pectoral region, and a first response vector for sensing a first response to the first excitation signal, the sensing the first response using a left ventricular electrode configured to be associated with a left ventricle and a pectoral electrode configured to be associated with a pectoral region.

In Example 9, the subject matter of any one of Examples 1-8 can optionally include the processor being configured to use the information about the change in the first tissue characteristic measurement over the period of time and the information about the change in the second tissue characteristic measurement over the period of time to provide an indication associated with how much fluid is present at the first location, wherein the first location is associated with a localized lung region, relative to how much fluid is present at the second location, wherein the second location is within the subject and associated with a global region that extends beyond the localized lung region.

Example 10 can include, or can optionally be combined with any one of Examples 1-9 to include subject matter that can include: providing a first measurement vector, within a subject, comprising a first excitation vector for providing a first excitation signal and a first response vector for sensing a first response to the first excitation signal; providing a second measurement vector, within the subject, comprising a second excitation vector for providing a second excitation signal and a second response vector for sensing a second response to the second excitation signal, wherein the second excitation vector is substantially orthogonal to the second response vector; repeatedly performing a first tissue characteristic measurement using the first measurement vector and to perform a second tissue characteristic measurement using the second measurement vector, and using information about a change in the first tissue characteristic measurement over a period of time and information about a change in the second tissue characteristic measurement over the period of time to provide an indication associated with how much fluid is present at an first location in the subject relative to how much fluid is present at a second location in the subject.

In Example 11, the subject matter of any one of Examples 1-10 can optionally further comprise providing implantable first electrodes configured for providing the first, measurement vector and providing implantable second electrodes configured for providing the second measurement vector.

In Example 12, the subject matter of any one of Examples 1-11 can optionally comprise using the information about the change in the first tissue characteristic measurement over the period of time and the information about the change in the second tissue characteristic measurement over the period of time to provide an indication associated with how much fluid is present at the first location, wherein the first location is associated with a pocket about an implantable medical device, relative to how much fluid is present at the second location, wherein the second location is within the subject but separated from the pocket about the implantable medical device.

In Example 13, the subject matter of any one of Examples 1-12 can optionally comprise using the information about the change in the first tissue characteristic measurement over the period of time and the information about the change in the second tissue characteristic measurement over the period of time to provide an indication of whether infection is present at the first location associated with the pocket about the implantable medical device.

In Example 14, the subject matter of any one of Examples 1-13 can optionally comprise using information about a first temperature at a location of the subject to provide the indication of whether infection is present at the first location associated with the pocket about the implantable medical device.

In Example 15, the subject matter of any one of Examples 1-14 can optionally comprise using information about a second temperature at a location of the subject that is different from the location associated with the first temperature to provide the indication of whether infection is present at the first location associated with the pocket about the implantable medical device.

In Example 16, the subject matter of any one of Examples 1-15 can optionally include the second measurement vector comprising a second excitation vector for providing a second excitation signal between a left ventricle region and a pectoral region, and a second response vector for sensing a second response to the second excitation signal between a left ventricle region and a right region, wherein the second excitation vector is substantially orthogonal to the second response vector.

In Example 17, the subject matter of any one of Examples 1-16 can optionally include at least one of: (a) the first measurement vector comprising a first excitation vector for providing a first excitation signal between a right ventricular region and a pectoral region, and a first response vector for sensing a first response to the first excitation signal, the sensing the first response between a right ventricular region and a pectoral region; (b) the first measurement vector comprising a first excitation vector for providing a first excitation signal between a right atrial region and a pectoral region, and a first response vector for sensing a first response to the first excitation signal, the sensing the first response between a right atrial region and a pectoral region; or (c) the first measurement vector comprising a first excitation vector for providing a first excitation signal between a left ventricular region and a pectoral region, and a first response vector for sensing a first response to the first excitation signal, the sensing the first response between a left ventricular region and a pectoral region.

In Example 18, the subject matter of any one of Examples 1-17 can optionally comprise using the information about the change in the first tissue characteristic measurement over the period of time and the information about the change in the second tissue characteristic measurement over the period of time to provide an indication associated with how much fluid is present at the first location, wherein the first location is associated with a localized lung region, relative to how much fluid is present at the second location, wherein the second location is within the subject and associated with a global region that extends beyond the localized lung region.

Example 19 can include, or can be combined with the subject matter of any one of Examples 1-18 to include subject matter including means for providing a first measurement vector, within a subject, comprising a first excitation vector for providing a first excitation signal and a first response vector for sensing a first response to the first excitation signal; means for providing a second measurement vector, within the subject, comprising a second excitation vector for providing a second excitation signal and a second response vector for sensing a second response to the second excitation signal, wherein the second excitation vector is substantially orthogonal to the second response vector; means for repeatedly performing a first tissue characteristic measurement using the first measurement vector and to perform a second tissue characteristic measurement using the second measurement vector; and means for using information about a change in the first tissue characteristic measurement over a period of time and information about a change in the second tissue characteristic measurement over the period of time to provide an indication associated with how much fluid is present at an first location in the subject relative to how much fluid is present at a second location in the subject.

In Example 20, the subject matter of any one of Examples 1-19 can optionally comprise a processor configured to use the information about the change in the first tissue characteristic measurement over the period of time and the information about the change in the second tissue characteristic measurement over the period of time to provide an indication associated with how much fluid is present at the first location, wherein the first location is associated with a pocket about an implantable medical device, relative to how much fluid is present at the second location, wherein the second location is within the subject but separated from the pocket about the implantable medical device. The processor can be configured to use the information about the change in the first tissue characteristic measurement over the period of time and the information about the change in the second tissue characteristic measurement over the period of time to provide an indication of whether infection is present at the first location associated with the pocket about the implantable medical device.

The examples can be combined with each other or with the other subject matter described herein in any combination or permutation. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 shows an example of a technique to determine whether fluid accumulation is present and, if so, whether such fluid accumulation is local to a pocket in which a CRM device electronics unit is implanted, which can be indicative of local pocket infection, hematoma or seroma, or the like.

DETAILED DESCRIPTION

The present inventors have recognized that using (1) an orthogonal measurement vector and (2) a non-orthogonal measurement vector, a relative measurement between (1) and (2) can be used to provide a more sensitive indication of fluid accumulation, such as to localize a region of fluid accumulation, or to distinguish between different regions of fluid accumulation.

Figure 1:
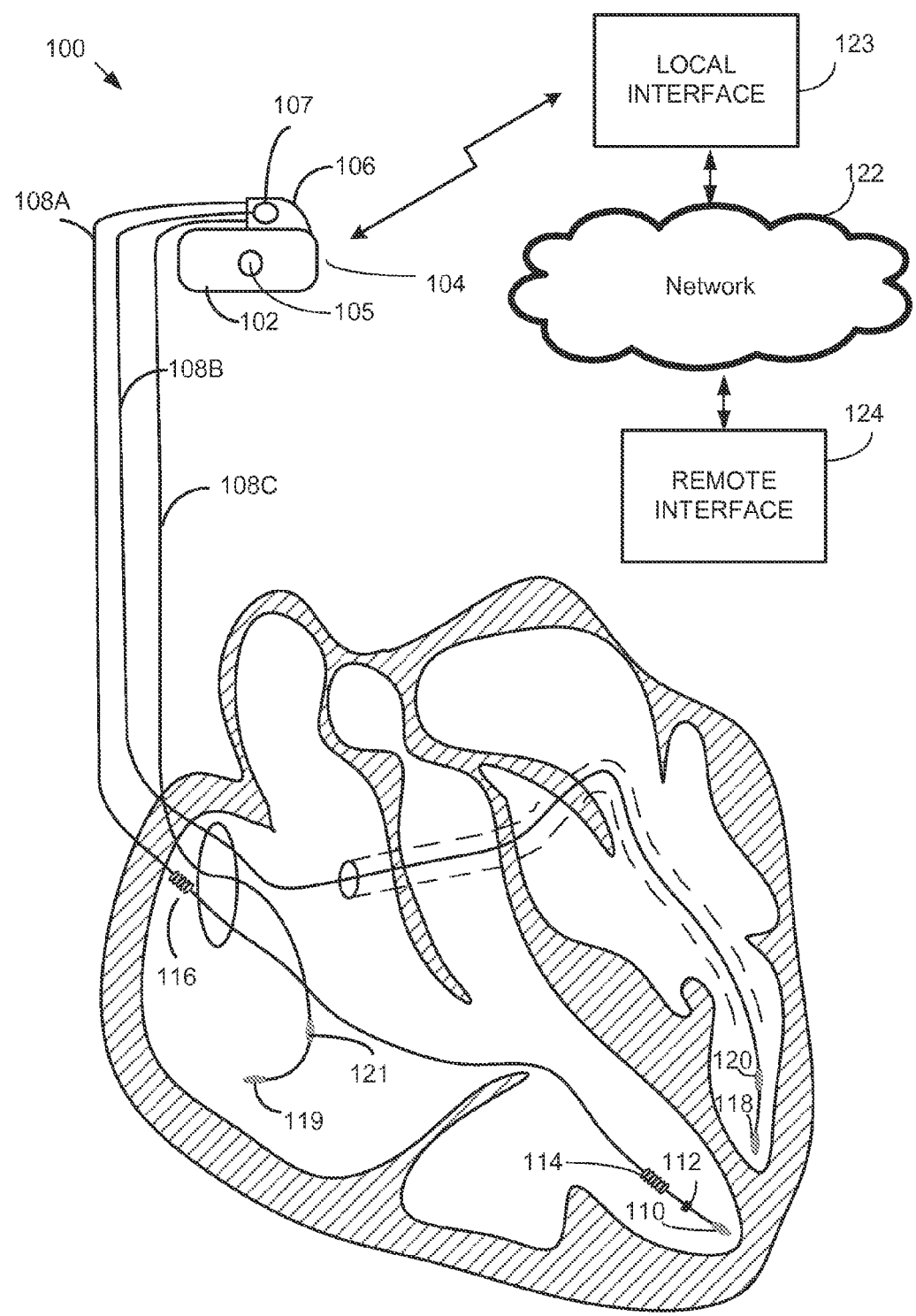
FIG. 1 shows an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular CS/LV lead 108B can extend from the SVC into the RA, through a coronary sinus (CS) into the coronary vasculature, such as near a portion of a left ventricle (LV). In an example, this second CS/LV lead 108B can include a distal electrode 118 and a proximal electrode 120, from which electrostimulation energies can be delivered or intrinsic electrical heart signals can be sensed. An intravascular right atrial (RA) lead 108C can extend from the SVC into the RA, and can include a distal electrode 119 and a proximal electrode 121. Other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

Figure 2:
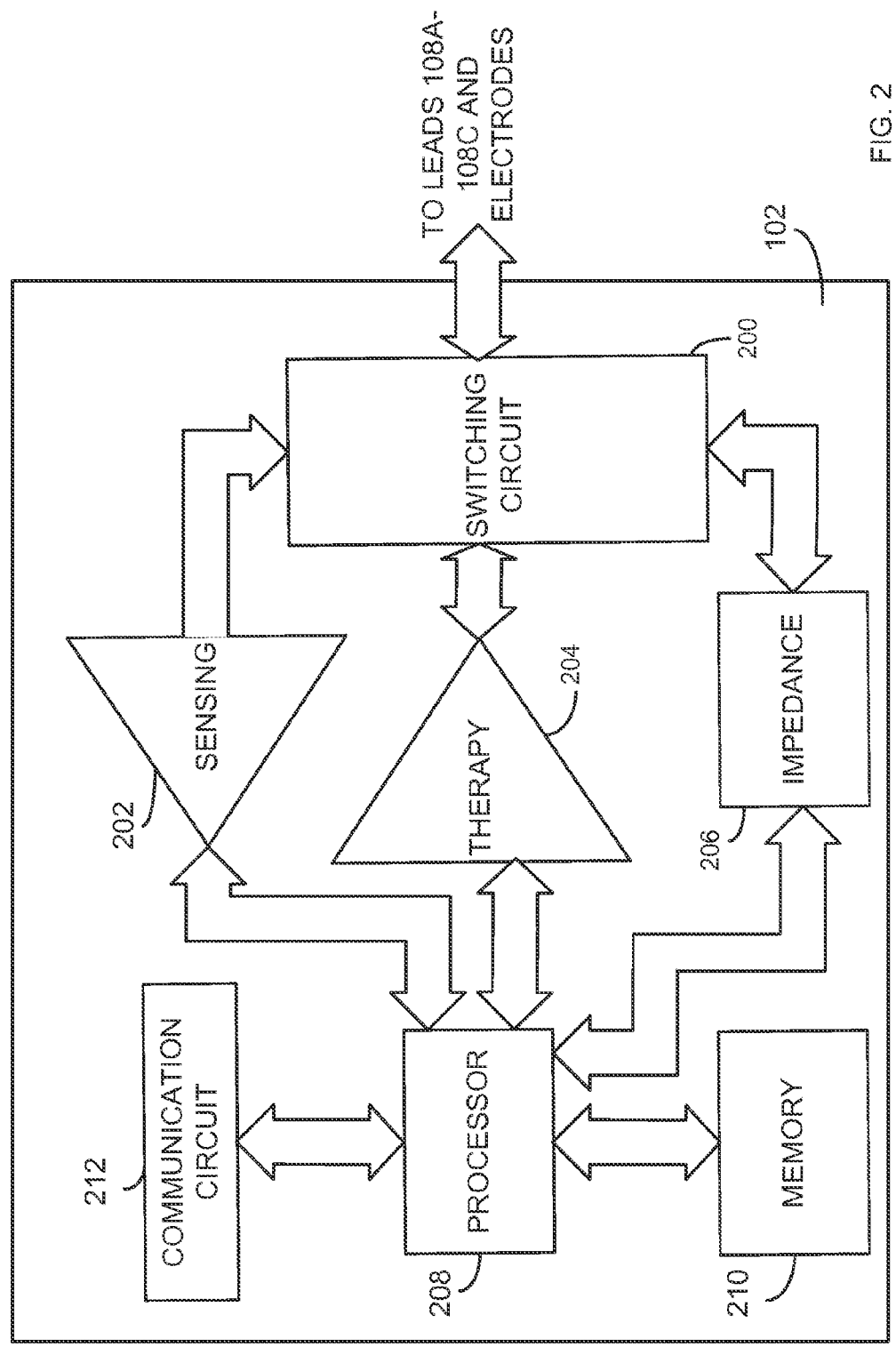
FIG. 2 shows an example of portions of the CRM device electronics unit.

FIG. 2 shows an example of portions of the CRM device electronics unit 102. In an example, this can include a switching circuit 200, such as for selectively connecting to the various electrodes such as on the leads 108A-B or elsewhere. A sensing circuit 202 can be selectively coupled to various electrodes by the switching circuit 200, and can include sense amplifiers, filter circuits, other circuits such as for sensing intrinsic electrical signals, such as intrinsic heart signals. A therapy circuit 204 can be selectively coupled to various electrodes by the switching circuit 200, and can include therapy energy generation circuitry (e.g., capacitive, inductive, or other) such as for generating, storing, or delivering an electrostimulation, cardioversion, defibrillation, or other energy. An impedance measurement circuit 206 can be selectively coupled to various electrodes by the switching circuit 200, such as for measuring a lead impedance, a tissue impedance, a regional or organ impedance, or other impedance. In an example, the sensing circuit 202, the therapy circuit 204, or the impedance circuit 206 can be coupled to a processor circuit 208. In an example, the processor 208 can perform instructions, such as for signal processing of signals derived by the sensing circuit 202 or the impedance circuit 206, or for controlling operation of the therapy circuit 204 or other operations of the CRM device 100. The processor 208 can also be coupled to or include a memory circuit 210, such as for storing or retrieving instructions or data, or a communication circuit 212, such as for communicating with the local interface 121.

Figure 3:
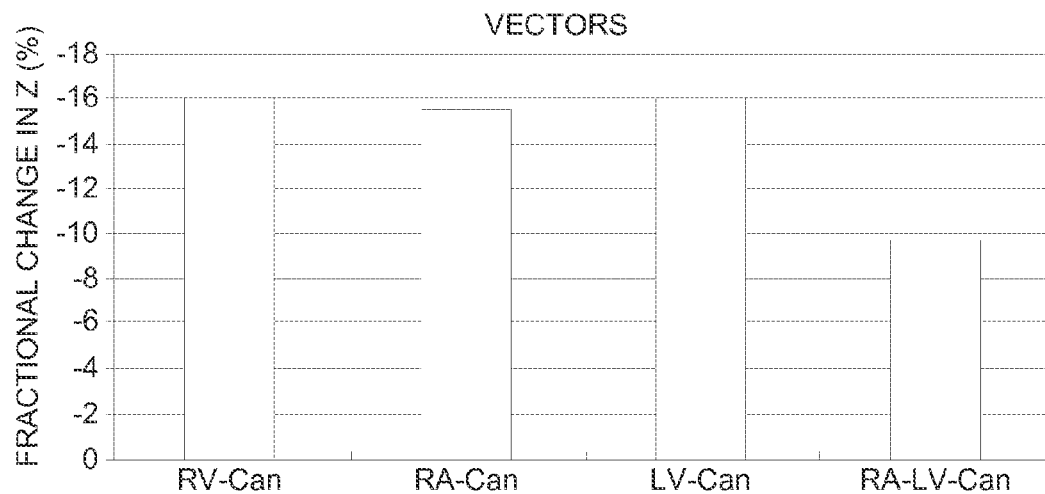
FIG. 3 is a graph illustrating examples of experimentally-observed data of the fractional change in impedance observed before and after injecting saline fluid into a pocket into which a CRM device electronics unit was implanted, with the graph illustrating four different impedance vector configurations that were used.

FIG. 3 is a graph illustrating examples of experimentally-observed data of the fractional change in impedance observed before and after injecting saline fluid into a pocket into which a CRM device electronics unit 102 was implanted, with the graph illustrating four different impedance vector configurations that were used. Such injection of saline into the pocket is believed to be at least somewhat representative of conditions that would be observed if the pocket became infected, leading to localized fluid accumulation in the pocket. The example of FIG. 3 shows impedance determined from: (1) an RV-Can (non-orthogonal) electrode configuration, in which both the excitation vector and the response vector are provided between an RV electrode (e.g., 110, 112, or 114) and a Can electrode (e.g., 107 or 106); (2) an RA-Can (non-orthogonal) electrode configuration, in which both the excitation and the response vector are provided between an RA electrode (e.g., 119 or 121) and a Can electrode (e.g., 107 or 106); (3) an LV-Can (non-orthogonal) electrode configuration, in which both the excitation and the response vector are provided between an CS/LV electrode (e.g., 118 or 120) and a Can electrode (e.g., 107 or 106); and (4) an RA-LV-Can (orthogonal) electrode configuration, in which the excitation vector is provided between a CS/LV electrode (e.g., 118 or 120) and a Can electrode (e.g., 107 or 106) and the response vector is provided between a CS/LV electrode (e.g., 118 or 120) and an RA electrode (e.g., 119 or 121).

In this example, the three non-orthogonal vectors exhibited a fractional impedance change of about 15%. The orthogonal vector exhibited a fractional impedance change of about 10%. Thus, the orthogonal vector was observed to be less sensitive to fluid accumulation around the pocket than the non-orthogonal vectors. The present inventors have recognized, among other things, that because of this relative difference, an orthogonal vector can be used together with a non-orthogonal vector to determine whether fluid accumulation is localized to the pocket or otherwise, as explained further below.

Figure 4:
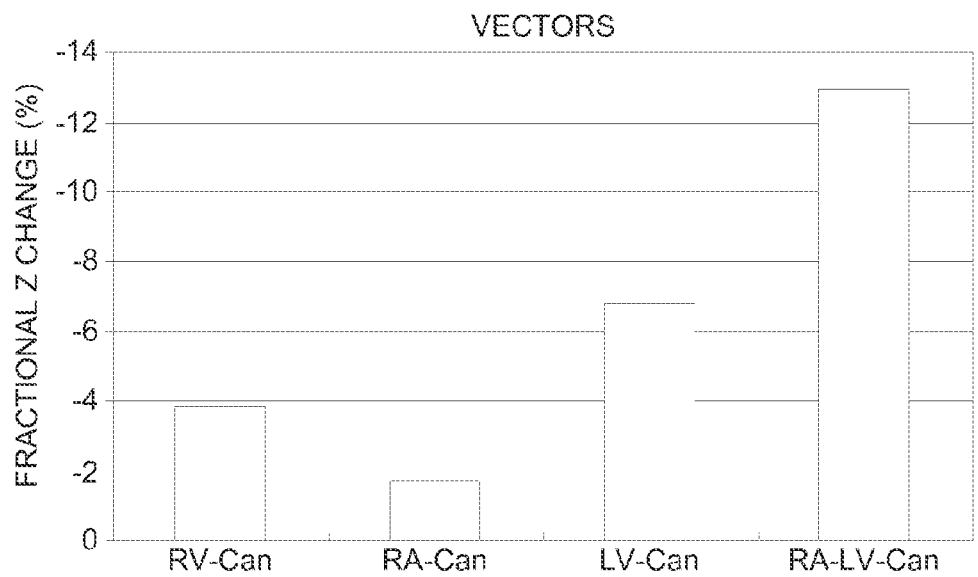
FIG. 4 is a graph illustrating experimental data indicating a fractional change in impedance resulting from lung fluid accumulation for the same four vectors as FIG. 3.

FIG. 4 is a graph illustrating experimental data indicating a fractional change in impedance resulting from lung fluid accumulation for the same four vectors as FIG. 3. Unlike the case of FIG. 3 for pocket fluid accumulation, the orthogonal vector exhibited a greater fractional change in impedance (about 13%) than the non-orthogonal vectors (about 2% to about 7%). Thus, as can be seen in FIG. 4, the orthogonal vector was observed to be more sensitive to pulmonary fluid accumulation than the non-orthogonal vectors. The present inventors have recognized, among other things, that because of this relative difference, an orthogonal vector can be used together with a non-orthogonal vector to determine whether fluid accumulation is localized to the lungs or otherwise, as explained further below.

Figure 5:
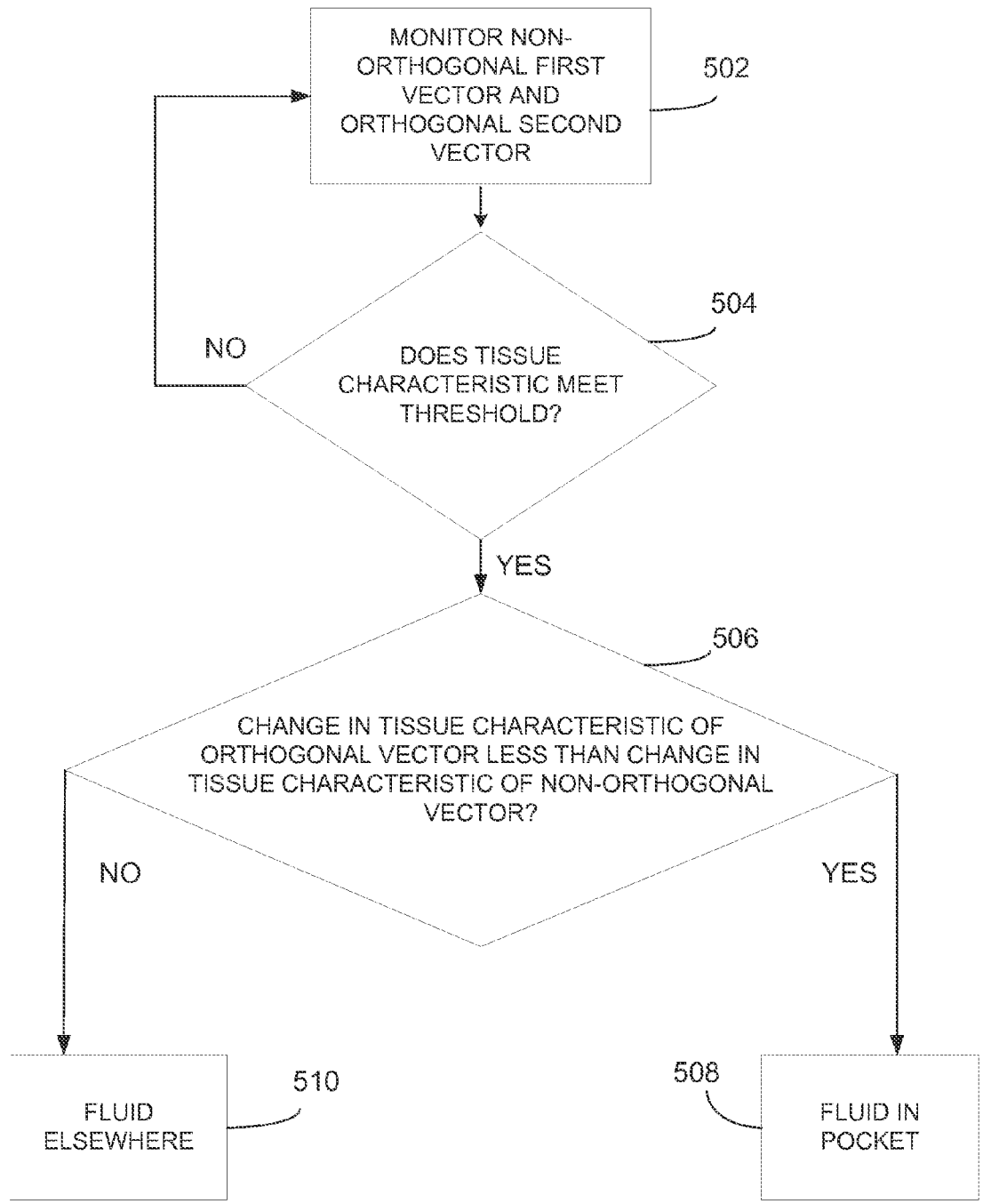

FIG. 5 shows an example of a technique to determine whether fluid accumulation is present and, if so, whether such fluid accumulation is local to a pocket in which a CRM device electronics unit 102 is implanted, which can be indicative of local pocket infection, hematoma or seroma, or the like. Infection rates are believed to be increasing faster than CRM device implant rates. Infection can result in device removal, antibiotic treatment, or both, and can be very costly. In an example, the technique of FIG. 5 can be performed all or in part by using the CRM device 100 shown in FIG. 1.

At 502, a non-orthogonal first measurement vector and an orthogonal second vector can be monitored (e.g., trended over an acute or chronic period of time). As illustrative examples, the non-orthogonal first measurement vector can include RV-Can, RA-Can, or LV-Can, and the orthogonal second measurement vector can include RA-LV-Can, some examples of such non-orthogonal and orthogonal measurement vectors are described above. The monitoring can include providing an excitation signal and measuring a response signal, such as to measure a tissue characteristic. In an example, the monitoring can include providing an excitation current of specified amplitude, and measuring a voltage response thereto, such as to provide an indication of tissue impedance.

At 504, it is determined whether a tissue characteristic meets a threshold. In an example, this can include detecting when a tissue impedance falls below a threshold value, indicating the presence of fluid accumulation. The threshold value need not be static or absolute, but can vary or be relative, such as an offset from a baseline long term value, for example. Detecting whether the tissue impedance falls below a threshold value can be determined using a single measurement vector, or using a weighted or other combination of multiple measurement vectors, such as non-orthogonal vectors, orthogonal vectors, or a combination thereof. The comparison to a threshold can use a single measurement or multiple measurements, such as an average or other central tendency of multiple measurements obtained during a specified period of time.

At 506, if it has been determined at 504 that the tissue characteristic meets a threshold value (e.g., fluid accumulation is present), then it can be determined at 506 whether a change in the tissue characteristic of the orthogonal vector is less than a change in the tissue characteristic of the non-orthogonal vector. For an example in which the tissue characteristic includes a tissue impedance, it can be determined at 506 whether a change in tissue impedance of the orthogonal vector is less than a change in tissue impedance of the non-orthogonal vector and, if so, then at 508, the fluid accumulation is declared to be associated with local fluid in the pocket, and otherwise, at 510, the fluid accumulation is declared to not be associated with local fluid in the pocket, but instead associated with fluid elsewhere (e.g., global fluid overload, pulmonary edema, etc.). Local fluid in the pocket can be a sign of pocket infection, hematoma, or seroma. Information about (or based on) whether the fluid accumulation is local to the pocket (e.g., fluid presence, fractional change in impedance, indication of infection, hematoma, or seroma, etc.) can be communicated to a user or automated process, such as to provide a diagnostic indication or for use in controlling a therapy provided by the CRM device 100, another implanted, ambulatory, or other medical device, or by a physician or other caregiver. Such communication can be internal to the electronics unit 102 of the CRM device 100, or can involve communication with the local interface 121 or with the remote interface 124. The acts described in FIG. 5 can be performed by the processor 208 or other circuitry in the electronics unit 102 of the CRM device 100, or by a processor or other circuitry associated with the local interface 121 or the remote interface 124, or using some combination of the CRM device 100, the local interface 121, or the remote interface 124.

At 506, determining whether a change in the tissue characteristic of an orthogonal vector is less than a change in the tissue characteristic of the non-orthogonal vector need not involve comparing absolute actual changes in the tissue characteristic. For example, where the tissue characteristic includes a tissue impedance, it can involve comparing a fractional change in the impedance of the orthogonal vector to a fractional change in the impedance of the non-orthogonal vector or can involve scaling the impedance of the non-orthogonal vector or the orthogonal vector.

As an illustrative example, the comparison can be expressed as:

$$\Delta Z_O/Z_O < \alpha \cdot \Delta Z_{NO}/Z_{NO}$$

where, in the above equation, $\Delta Z_O$ represents the change in impedance of the orthogonal vector, $Z_O$ represents a baseline (e.g., long term) value of the impedance of the orthogonal vector, $\Delta Z_O/Z_O$ represents a fractional change in impedance of the orthogonal vector relative to its baseline value, $\Delta Z_{NO}$ represents the change in impedance of the non-orthogonal vector, $Z_{NO}$ represents a baseline (e.g., long term) value of the impedance of the non-orthogonal vector, $\Delta Z_{NO}/Z_{NO}$ represents a fractional change in impedance of the non-orthogonal vector relative to its baseline value, and $\alpha$ represents a specified scaling factor for the comparison to be applied to a specified side of the relationship of the above comparison. This example is merely illustrative of the type of comparison that can be made. Other comparisons, or variations on the above comparison can be made. For example, where the decrease in fluid impedance is expected to exhibit a slower time-course, a cumulative sum of difference (e.g., summing impedance deviations from the baseline over a specified time period) or like technique can be used to determine the change the non-orthogonal and orthogonal impedances.

Figure 6:
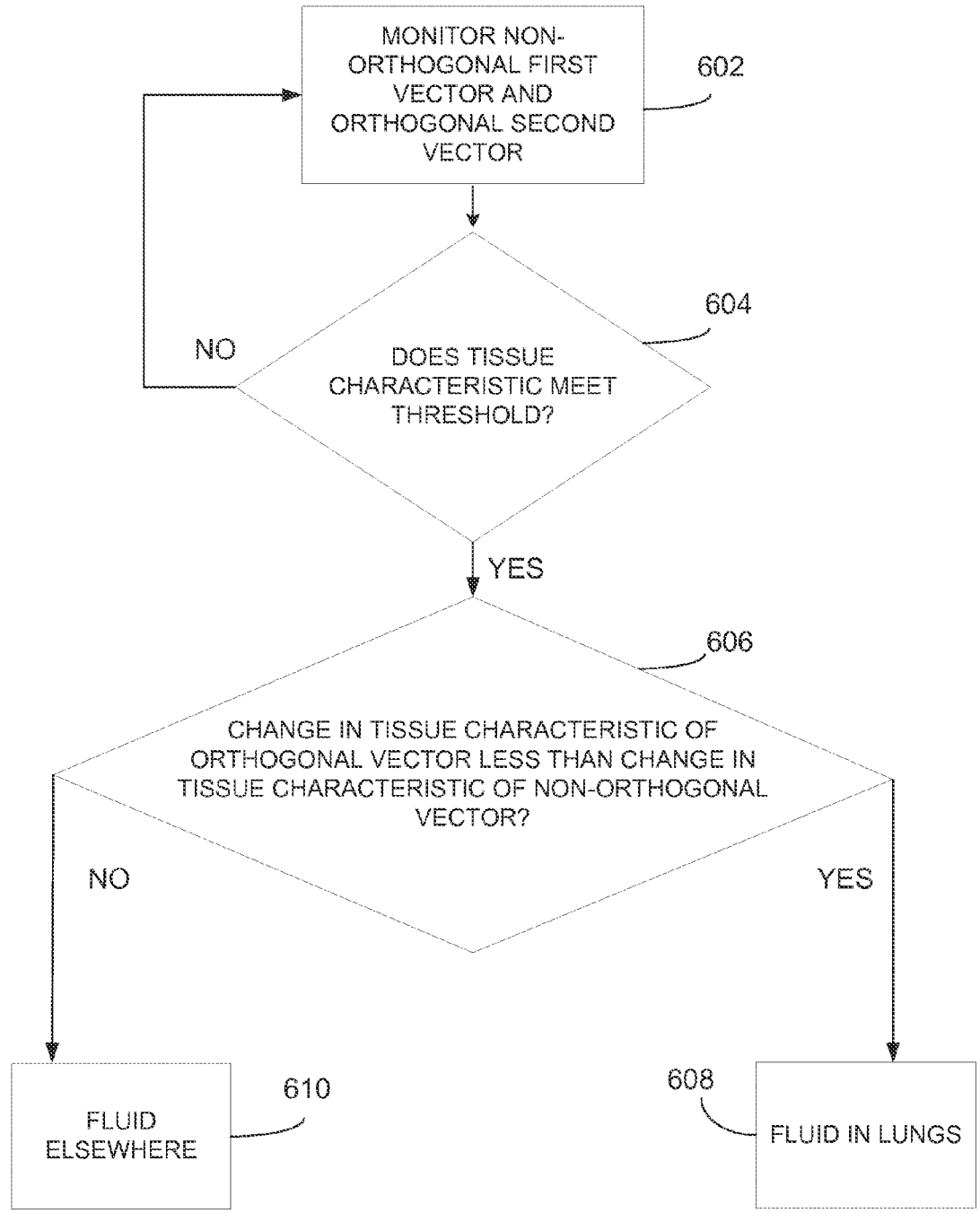
FIG. 6 shows an example of a technique to determine whether fluid accumulation is present and, if so, whether such fluid accumulation is local to a lung region or indicative of a more global fluid overload condition.

FIG. 6 shows an example of a technique to determine whether fluid accumulation is present and, if so, whether such fluid accumulation is local to a lung region or indicative of a more global fluid overload condition. This can be useful to distinguish between pneumonia, which can be indicated by fluid accumulation that is local to a lung region, and global fluid overload, which can be indicative of a CHF decompensation episode. Pneumonia is a risk factor for CHF patients and is also a relatively prevalent (e.g., 15%) comorbidity for CHF patients being admitted for hospitalization. In an example, the technique of FIG. 6 can be performed all or in part by using the CRM device 100 shown in FIG. 1.

At 602, a non-orthogonal first measurement vector and an orthogonal second vector can be monitored (e.g., trended over an acute or chronic period of time). In the example of FIG. 6, the non-orthogonal first measurement vector can include a vector that is substantially local within the heart (e.g., using RV tip electrode 110 and RV Coil electrode 114 for delivering an excitation and measuring the response) and the orthogonal second measurement vector can include RA-LV-Can, such as described above. The monitoring can include providing an excitation signal and measuring a response signal, such as to measure a tissue characteristic. In an example, the monitoring can include providing an excitation current of specified amplitude, and measuring a voltage response thereto, such as to provide an indication of tissue impedance.

At 604, it is determined whether a tissue characteristic meets a threshold. In an example, this can include detecting when a tissue impedance falls below a threshold value, indicating the presence of fluid accumulation. The threshold value need not be static or absolute, but can vary or be relative, such as an offset from a baseline long term value, for example. Detecting whether the tissue impedance falls below a threshold value can be determined using a single measurement vector, or using a weighted or other combination of multiple measurement vectors, such as non-orthogonal vectors, orthogonal vectors, or a combination thereof. The comparison to a threshold can use a single measurement or multiple measurements, such as an average or other central tendency of multiple measurements obtained during a specified period of time.

At 606, if it has been determined at 604 that the tissue characteristic meets a threshold value (e.g., fluid accumulation is present), then it can be determined at 606 whether a change in the tissue characteristic of the orthogonal vector is less than a change in the tissue characteristic of the non-orthogonal vector. For an example in which the tissue characteristic includes a tissue impedance, it can be determined at 606 whether a change in tissue impedance of the orthogonal vector is less than a change in tissue impedance of the non-orthogonal vector and, if so, then at 608, the fluid accumulation is declared to be associated with local fluid in the lungs, and otherwise, at 610, the fluid accumulation is declared to not be associated with local fluid in the lungs (e.g., such as can arise from pneumonia), but instead associated with fluid elsewhere (e.g., global fluid overload such as associated with a CHF decompensation episode. Information about (or based on) whether the fluid accumulation is local to the lungs (e.g., fluid presence, fractional change in impedance, indication of pneumonia, CHF decompensation, etc.) can be communicated to a user or automated process, such as to provide a diagnostic indication or for use in controlling a therapy provided by the CRM device 100 (e.g., cardiac resynchronization therapy (CRT)), by another implanted, ambulatory, or other medical device, or by a physician or other caregiver. Such communication can be internal to the electronics unit 102 of the CRM device 100, or can involve communication with the local interface 121 or with the remote interface 124. The acts described in FIG. 6 can be performed by the processor 208 or other circuitry in the electronics unit 102 of the CRM device 100, or by a processor or other circuitry associated with the local interface 121 or the remote interface 124, or using some combination of the CRM device 100, the local interface 121, or the remote interface 124.

At 606, determining whether a change in the tissue characteristic of an orthogonal vector is less than a change in the tissue characteristic of the non-orthogonal vector need not involve comparing absolute actual changes in the tissue characteristic. For example, where the tissue characteristic includes a tissue impedance, it can involve comparing a fractional change in the impedance of the orthogonal vector to a fractional change in the impedance of the non-orthogonal vector or can involve scaling the impedance of the non-orthogonal vector or the orthogonal vector.

As an illustrative example, the comparison can be expressed as:

$$\Delta Z_O/Z_O < \alpha \cdot \Delta Z_{NO}/Z_{NO}$$

where, in the above equation, $\Delta Z_O$ represents the change in impedance of the orthogonal vector, $Z_O$ represents a baseline (e.g., long term) value of the impedance of the orthogonal vector, $\Delta Z_O/Z_O$ represents a fractional change in impedance of the orthogonal vector relative to its baseline value, $\Delta Z_{NO}$ represents the change in impedance of the non-orthogonal vector, $Z_{NO}$ represents a baseline (e.g., long term) value of the impedance of the non-orthogonal vector, $\Delta Z_{NO}/Z_{NO}$ represents a fractional change in impedance of the non-orthogonal vector relative to its baseline value, and $\alpha$ represents a specified scaling factor for the comparison to be applied to a specified side of the relationship of the above comparison.

As described above, in the example of FIG. 6, the non-orthogonal first measurement vector can include a vector that is substantially local within the heart (e.g., using RV tip electrode 110 and RV Coil electrode 114 for delivering an excitation and measuring the response) and the orthogonal second measurement vector can include RA-LV-Can, such as described above.

This example is merely illustrative of the type of comparison that can be made. Other comparisons, or variations on the above comparison can be made. For example, where the decrease in fluid impedance is expected to exhibit a slower time-course, a cumulative sum of difference (e.g., summing impedance deviations from the baseline over a specified time period) or like technique can be used to determine the change the non-orthogonal and orthogonal impedances.

In an example, the techniques of FIGS. 5 and 6 can be used together. For example, the technique of FIG. 5 can be used to determine whether a fluid accumulation is due to local fluid accumulating in the pocket or something else, such as described above. If something else, then the technique of FIG. 6 can be used to further determine whether the fluid accumulation is due to fluid accumulating in the lungs (e.g., from pneumonia) or something else, such as a global fluid overload (e.g., from CHF decompensation).

More generally, the examples of techniques described above with respect to FIGS. 5 and 6 can be applied more generally to detect various conditions such as by using a differential tissue characteristic between an orthogonal vector and a non-orthogonal vector. Further, various orthogonal and non-orthogonal vectors can be used together in various permutations and combinations. Table 1 below lists some examples.

TABLE 1

Examples of Physiological Conditions Detectable using a Non-Orthogonal Vector and an Orthogonal Vector

| Condition | Non-Orthogonal Vector | Orthogonal Vector |
|---|---|---|
| Pocket Fluid (e.g., from infection, hematoma, or seroma) | LV (e.g., 118, 120)-Can (e.g., 105, 107) | RA (e.g., 119, 121)-LV (e.g., 118, 120)-Can (e.g., 105, 107) |
| Pocket Fluid (e.g., from infection, hematoma, or seroma) | LV (e.g., 118, 120)-Can (e.g., 105, 107) | RV (e.g., 110, 112, 114)-LV (e.g., 118, 120)-Can (e.g., 105, 107) |
| Pocket Fluid (e.g., from infection, hematoma, or seroma) | LV (e.g., 118, 120)-Can (e.g., 105, 107) | SVC (e.g., 116)-LV (e.g., 118, 120)-Can (e.g., 105, 107) |
| Pocket Fluid (e.g., from infection, hematoma, or seroma) | LV (e.g., 118, 120)-Can (e.g., 105, 107) | RA (e.g., 119, 121)-Can (e.g., 105, 107)-LV (e.g., 118, 120) |
| Pocket Fluid (e.g., from infection, hematoma, or seroma) | RV (e.g., 110, 112, 114)-Can (e.g., 105, 107) | RA (e.g., 119, 121)-Can (e.g., 105, 107)-LV (e.g., 118, 120) |
| Pocket Fluid (e.g., from infection, hematoma, or seroma) | RA (e.g., 119, 121)-Can (e.g., 105, 107) | SVC (e.g., 116)-Can (e.g., 105, 107)-LV (e.g., 118, 120) |
| Pericardial Fluid (e.g., from pericardial effusion or pericarditis) | RV (e.g., 110, 112, 114)-LV (e.g., 118, 120) | RA (e.g., 119, 121)-RV (e.g., 110, 112, 114)-LV (e.g., 118, 120) |
| Pericardial Fluid (e.g., from pericardial effusion or pericarditis) | RA (e.g., 1119, 121)-RV(e.g., 110, 112, 114) | RA (e.g., 119, 121)-RV (e.g., 110, 112, 114)-LV (e.g., 118, 120) |
| Pericardial Fluid (e.g., from pericardial effusion or pericarditis) | RV (e.g., 110, 112, 114)-LV (e.g., 118, 120) | SVC (e.g., 116)-RV (e.g., 110, 112., 114)-LV (e.g., 118, 120) |
| Pericardial Fluid (e.g., from pericardial effusion or pericarditis) | SVC (e.g., 116)-RV (e.g., 110, 112, 114) | SVC (e.g., 116)-RV (e.g., 110, 112, 114)-LV (e.g., 118, 120) |
| Pulmonary Fluid (e.g., from pneumonia or pulmonary congestion) | LV (e.g., 118, 120)-Can (e.g., 105, 107) | RA (e.g., 119, 121)-LV (e.g., 118, 120)-Can (e.g., 105, 107) |
| Pulmonary Fluid (e.g., from pneumonia or pulmonary congestion) | RA (e.g., 119, 121)-Can (e.g., 105, 107) | RA (e.g., 119, 121)-LV (e.g., 118, 120)-Can (e.g., 105, 107) |
| Pulmonary Fluid (e.g., from pneumonia or pulmonary congestion) | RV (e.g., 110, 112, 114)-Can (e.g., 105, 107) | RA (e.g., 119, 121)-LV (e.g., 118, 120)-Can (e.g., 105, 107) |
| Hemodilution | RV (e.g., 110, 112, 114)-Can (e.g., 105, 107) | RA (e.g., 119, 121)-RV (e.g., 110, 112, 114)-Can (e.g., 105, 107) |
| Hemodilution | RA (e.g., 119, 121)-Can(e.g., 105, 107) | RV (e.g., 110, 112, 114)-RA (e.g., 119, 121)-Can (e.g., 105, 107) |

In Table 1, the orthogonal vectors use a measurement vector comprising an excitation vector that is different than the response vector. For a tripolar orthogonal vector, the configuration can be denoted (x-y-z), such as written in the examples of Table 1, where the excitation signal is provided between the electrodes y and z and the response signal is measured between electrodes x and y. In a vice-versa example, the excitation signal can be provided between the electrodes x and y and the response signal can be measured between the electrodes y and z.

In the above examples, the orthogonal and non-orthogonal vectors have been explained, for illustrative clarity, with respect to the case in which the electronics unit 102 of the CRM device 100 is implanted in a pocket in the left pectoral region of the subject. However, this is not always the case. In other examples, the electronics unit 102 of the CRM device 100 can be implanted in a pocket in the right pectoral region, or abdominally, and the orthogonal vectors and non-orthogonal vectors can be adjusted accordingly for such different implant locations of the electronics unit 102 of the CRM device 100.

In an example, for a left-side pectorally implanted electronics unit 102 of the CRM device 100, examples of orthogonal vectors to the pocket location of the implanted electronics unit 102 of the CRM device 100 can include: (1) LV-Can-RA; or (2) RV-Can-RA. For a right side pectorally implanted electronics unit 102 of the CRM device 100, examples of orthogonal vectors to the pocket location of the implanted electronics unit 102 of the CRM device 100 can include (1) RV-Can-RA; or (2) LV-Can-RA; or (3) LV-Can-RV.

In an example that includes a lead-connected or other pulmonary artery pressure (PAP) sensor that includes a pulmonary artery (PA) electrode, this provides more possibilities for providing orthogonal vectors, for a left-side implanted electronics unit 102 or a right-side implanted electronics unit 102, e.g., PA-Can-X, wherein X can include an intracardiac electrode, such as any of the intracardiac electrodes described above.

In an example, for a left-side pectorally implanted electronics unit 102 of the CRM device 100, examples of orthogonal vectors to the heart can include: (1) Can-RV-RA; or (2) Can-LV-RA. For a right side pectorally implanted electronics unit 102 of the CRM device 100, examples of orthogonal vectors to the heart can include (1) Can-RV-LV; or (2) Can-LV-RV (where LV can represent any one of the different electrodes that are typically associated with the left ventricle).

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third,"

etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A system comprising:
   a tissue impedance measurement circuit configured to sense a first tissue impedance measurement using a first impedance measurement vector, and to sense a second tissue impedance measurement using a different second impedance measurement vector, wherein:
      the first impedance measurement vector includes a first excitation vector for providing a first excitation signal, and a first response vector for sensing a first response to the first excitation signal, the first excitation vector being non-orthogonal to the first response vector; and
      the second impedance measurement vector includes a second excitation vector for providing a second excitation signal, and a second response vector for sensing a second response to the second excitation signal, the second excitation vector being substantially orthogonal to the second response vector;
   a detector circuit, communicatively coupled to the tissue impedance measurement circuit, configured to determine a change in the first tissue impedance measurement over a period of time and a change in the second tissue impedance measurement over the period of time, and to generate an indication of fluid accumulation at a body location using a comparison between the change in the first tissue impedance measurement and the change in the second tissue impedance measurement.

2. The system of claim 1, wherein the indication of fluid accumulation includes an indication of fluid accumulation at a lung region, and the detector circuit is further configured to detect a heart failure decompensation event using at least the indication of fluid accumulation.

3. The system of claim 1, wherein the change in the first tissue impedance measurement includes a fractional change from a baseline first tissue impedance measurement, and the change in the second tissue impedance measurement includes a fractional change from a baseline second tissue impedance measurement.

4. The system of claim 1, wherein the detector circuit is configured to generate the indication of fluid accumulation in response to a relative indication between the change in the second tissue impedance measurement and the change in the first tissue impedance exceeding a specified threshold.

5. The system of claim 1, wherein the detector circuit is configured to compute a weighed combination of the change in the first tissue impedance measurement and the change in the second tissue impedance measurement, and to generate the indication of fluid accumulation in response to the weighted combination meeting a specified criterion.

6. The system of claim 1, wherein the second impedance measurement vector comprises:
   the second excitation vector provided between a left ventricular electrode configured to be associated with a left ventricle and a pectoral electrode configured to be associated with a pectoral region; and
   the second response vector provided between a left ventricular electrode configured to be associated with the left ventricle and a right atrial electrode configured to be associated with a right atrium.

7. The system of claim 1, wherein the second impedance measurement vector comprises:
   the second excitation vector provided between a right ventricular electrode configured to be associated with a right ventricle and a pectoral electrode configured to be associated with a pectoral region; and
   the second response vector provided between a right ventricular electrode configured to be associated with the right ventricle and a right atrial electrode configured to be associated with a right atrium.

8. The system of claim 1, wherein the second impedance measurement vector comprises:
   the second excitation vector provided between a pulmonary artery electrode configured to be associated with a pulmonary artery and a pectoral electrode configured to be associated with a pectoral region; and
   the second response vector provided between a pulmonary artery electrode configured to be associated with the pulmonary artery and a right atrial electrode configured to be associated with a right atrium.

9. The system of claim 1, wherein at least one of:
   the first impedance measurement vector comprises the first excitation vector provided between a right ventricular electrode configured to be associated with a right ventricle and a pectoral electrode configured to be associated with a pectoral region, and the first response vector provided between a right ventricular electrode configured to be associated with a right ventricle and a pectoral electrode configured to be associated with a pectoral region;
   the first impedance measurement vector comprises the first excitation vector provided between a right atrial electrode configured to be associated with a right atrium and a pectoral electrode configured to be associated with a pectoral region, and the first response vector provided between a right atrial electrode configured to be associated with a right atrium and a pectoral electrode configured to be associated with a pectoral region; or the first impedance measurement vector comprises the first excitation vector provided between a left ventricular electrode configured to be associated with a left ventricle and a pectoral electrode configured to be associated with a pectoral region, and the first response vector provided between a left ventricular electrode configured to be associated with a left ventricle and a pectoral electrode configured to be associated with a pectoral region.

10. The system of claim 1, further comprising at least one temperature sensor configured to sense temperature of at a body location, wherein the detector is configured to generate the indication of fluid accumulation further in response to the sensed temperature falling within a specified range.

11. The system of claim 1, further comprising a therapy delivery circuit configured to deliver a therapy programmed using at least the indication of fluid accumulation.

12. The system of claim 1, wherein the second impedance measurement vector includes the second excitation vector provided between a first right ventricular electrode and a left ventricular electrode, and the second response vector provided between a second right ventricular electrode and an electrode configured to be associated with superior vena cava.

13. A method for assessing fluid status at a body location using a medical apparatus, comprising:
sensing a first tissue impedance measurement, including applying a first excitation signal to a first excitation vector, and sensing from a first response vector a first response to the first excitation signal, the first excitation vector being non-orthogonal to the first response vector;
sensing a second tissue impedance measurement, including applying a second excitation signal to a second excitation vector, and sensing from a second response vector a second response to the second excitation signal, the second excitation vector being substantially orthogonal to the second response vector;
determining a relative indication between a change in the second tissue impedance measurement and a change in the first tissue impedance; and
generating an indication of fluid accumulation at the body location in response to the relative indication exceeding a specified threshold.

14. The method of claim 13, further comprising detecting a heart failure decompensation event using at least the indication of fluid accumulation, wherein the indication of fluid accumulation includes an indication of fluid accumulation at a lung region.

15. The method of claim 13, wherein generating the indication of fluid accumulation includes determining a change in the first tissue impedance measurement over a period of time and a change in the second tissue impedance measurement over the period of time, and generating the indication of fluid accumulation using a comparison between the change in the first tissue impedance measurement and the change in the second tissue impedance measurement.

16. The method of claim 13, wherein sensing the second tissue impedance measurement includes applying the second excitation signal between a left ventricular electrode configured to be associated with a left ventricle and a pectoral electrode configured to be associated with a pectoral region, and sensing the second response between a left ventricular electrode configured to be associated with the left ventricle and a right atrial electrode configured to be associated with a right atrium.

17. The method of claim 13, wherein sensing the second tissue impedance measurement includes applying the second excitation signal between a pulmonary artery electrode configured to be associated with a pulmonary artery and a pectoral electrode configured to be associated with a pectoral region, and sensing the second response between a pulmonary artery electrode configured to be associated with the pulmonary artery and a right atrial electrode configured to be associated with a right atrium.

18. The method of claim 13, wherein sensing the first tissue impedance measurement includes at least one of:
applying the first excitation signal between a right ventricular electrode configured to be associated with a right ventricle and a pectoral electrode configured to be associated with a pectoral region, and sensing the first response between a right ventricular electrode configured to be associated with a right ventricle and a pectoral electrode configured to be associated with a pectoral region;
applying the first excitation signal between a right atrial electrode configured to be associated with a right atrium and a pectoral electrode configured to be associated with a pectoral region, and sensing the first response between a right atrial electrode configured to be associated with a right atrium and a pectoral electrode configured to be associated with a pectoral region; or
applying the first excitation signal between a left ventricular electrode configured to be associated with a left ventricle and a pectoral electrode configured to be associated with a pectoral region, and sensing the first response between a left ventricular electrode configured to be associated with a left ventricle and a pectoral electrode configured to be associated with a pectoral region.

19. The method of claim 13, further comprising delivering a therapy according to at least one therapy parameter, the at least one therapy parameter programmed using at least the indication of fluid accumulation.

20. A system comprising:
a tissue impedance measurement circuit configured to sense a first tissue impedance measurement using a first impedance measurement vector, and to sense a second tissue impedance measurement using a different second impedance measurement vector, wherein:
the first impedance measurement vector includes a first excitation vector for providing a first excitation signal, and a first response vector for sensing a first response to the first excitation signal, the first excitation vector being non-orthogonal to the first response vector; and
the second impedance measurement vector includes a second excitation vector for providing a second excitation signal, and a second response vector for sensing a second response to the second excitation signal, the second excitation vector being substantially orthogonal to the second response vector;
a detector circuit, communicatively coupled to the tissue impedance measurement circuit, configured to generate an indication of fluid accumulation at a body location using both the first and second tissue impedance measurements;

wherein the second excitation vector is provided between a pulmonary artery electrode configured to be associated with a pulmonary artery and a pectoral electrode configured to be associated with a pectoral region; and wherein the second response vector is provided between a pulmonary artery electrode configured to be associated with the pulmonary artery and a right atrial electrode configured to be associated with a right atrium.

* * * * *